US009592103B2

(12) United States Patent
Taub et al.

(10) Patent No.: US 9,592,103 B2
(45) Date of Patent: *Mar. 14, 2017

(54) VIRTUAL ORTHODONTIC TREATMENT

(71) Applicant: ALIGN TECHNOLOGY, INC., San Jose, CA (US)

(72) Inventors: Eldad Taub, Reut (IL); Avi Kopelman, Tenafly, NJ (US)

(73) Assignee: Align Technology, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/166,073

(22) Filed: May 26, 2016

(65) Prior Publication Data

US 2016/0270881 A1    Sep. 22, 2016

Related U.S. Application Data

(63) Continuation of application No. 12/967,347, filed on Dec. 14, 2010, now Pat. No. 9,375,293, which is a (Continued)

(30) Foreign Application Priority Data

Dec. 30, 1997    (IL) .......................................... 122807

(51) Int. Cl.
*A61C 3/00*    (2006.01)
*A61C 7/00*    (2006.01)
(Continued)

(52) U.S. Cl.
CPC ................ *A61C 7/002* (2013.01); *A61C 7/00* (2013.01); *A61C 7/12* (2013.01); *G06F 19/3437* (2013.01); *G06N 5/046* (2013.01); *G06N 99/005* (2013.01)

(58) Field of Classification Search
CPC .... A61C 7/002; G06F 19/3437; G06N 5/046; G06N 99/005
See application file for complete search history.

(56) References Cited

U.S. PATENT DOCUMENTS

| 2,467,432 A | 4/1949 | Kesling |
| 3,407,500 A | 10/1968 | Kesling |

(Continued)

FOREIGN PATENT DOCUMENTS

| AU | 3031677 A | 5/1979 |
| AU | 517102 B2 | 7/1981 |

(Continued)

OTHER PUBLICATIONS

AADR. American Association for Dental Research, Summary of Activities, Mar. 20-23, 1980, Los ngeles, CA, p. 195.
(Continued)

*Primary Examiner* — Heidi M Eide
(74) *Attorney, Agent, or Firm* — Wilson Sonsini Goodrich & Rosati

(57) ABSTRACT

A method for virtual orthodontic treatment is provided in which a virtual set of orthodontic components is associated, in a virtual space, with a first virtual three-dimensional image of teeth, and then by a set of rules which define the effect of the set of components' teeth, the effect of the virtual treatment can be computed. This virtual treatment can be used to predict the results of a real-life orthodontic treatment as to design such a treatment.

20 Claims, 9 Drawing Sheets

Related U.S. Application Data continuation of application No. 11/889,111, filed on Aug. 9, 2007, now Pat. No. 7,866,978, which is a continuation of application No. 10/749,388, filed on Jan. 2, 2004, now Pat. No. 7,275,930, which is a continuation of application No. 09/591,757, filed on Jun. 12, 2000, now Pat. No. 6,739,869, which is a continuation of application No. PCT/IL98/00593, filed on Dec. 7, 1998.

(51) Int. Cl.
*A61C 7/12* (2006.01)
*G06F 19/00* (2011.01)
*G06N 5/04* (2006.01)
*G06N 99/00* (2010.01)

(56) References Cited

U.S. PATENT DOCUMENTS

| | | |
|---|---|---|
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,464,349 A | 11/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |

(56) References Cited

U.S. PATENT DOCUMENTS

| | | | |
|---|---|---|---|
| 6,217,334 | B1 | 4/2001 | Hultgren |
| 6,244,861 | B1 | 6/2001 | Andreiko et al. |
| 6,309,215 | B1 | 10/2001 | Phan et al. |
| 6,315,553 | B1 | 11/2001 | Sachdeva et al. |
| 6,322,359 | B1 | 11/2001 | Jordan et al. |
| 6,334,853 | B1 | 1/2002 | Kopelman et al. |
| 6,350,120 | B1 | 2/2002 | Sachdeva et al. |
| 6,382,975 | B1 | 5/2002 | Poirier |
| 6,398,548 | B1 | 6/2002 | Muhammad et al. |
| 6,402,707 | B1 | 6/2002 | Ernst |
| 6,471,511 | B1 | 10/2002 | Chishti et al. |
| 6,482,298 | B1 | 11/2002 | Bhatnagar |
| 6,524,101 | B1 | 2/2003 | Phan et al. |
| 6,554,611 | B2 | 4/2003 | Chishti et al. |
| 6,572,372 | B1 | 6/2003 | Phan et al. |
| 6,629,840 | B2 | 10/2003 | Chishti et al. |
| 6,705,863 | B2 | 3/2004 | Phan et al. |
| 6,722,880 | B2 | 4/2004 | Chishti et al. |
| 6,739,869 | B1 | 5/2004 | Taub et al. |
| 7,275,930 | B2 | 10/2007 | Taub et al. |
| 2002/0006597 | A1 | 1/2002 | Andreiko et al. |
| 2003/0009252 | A1 | 1/2003 | Pavlovskaia et al. |
| 2003/0139834 | A1 | 7/2003 | Nikolskiy et al. |
| 2003/0224311 | A1 | 12/2003 | Cronauer |
| 2004/0128010 | A1 | 7/2004 | Pavlovskaia et al. |
| 2005/0055118 | A1 | 3/2005 | Nikolskiy et al. |
| 2011/0082669 | A1 | 4/2011 | Taub et al. |

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| ES | 463897 | 1/1980 |
| FR | 2369828 A1 | 6/1978 |
| FR | 2652256 A1 | 3/1991 |
| GB | 15500777 | 8/1979 |
| JP | 53-058191 | 5/1978 |
| JP | 04-028359 | 1/1992 |
| JP | 5-168654 A | 7/1993 |
| JP | 5-261124 A | 10/1993 |
| JP | 7-222759 A | 8/1995 |
| JP | 8-168499 A | 7/1996 |
| JP | 08-508174 | 9/1996 |
| JP | 8-280715 A | 10/1996 |
| WO | WO 90/08512 A1 | 8/1990 |
| WO | WO 91/04713 A1 | 4/1991 |
| WO | WO 94/10935 A1 | 5/1994 |
| WO | WO 97/03622 A1 | 2/1997 |
| WO | WO 98/32394 A1 | 7/1998 |
| WO | WO 98/44865 A1 | 10/1998 |
| WO | WO 98/58596 A1 | 12/1998 |
| WO | WO 01/80761 A2 | 11/2001 |

OTHER PUBLICATIONS

Alcaniz, et al, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler et al., "Analysis of 3-D Data for Comparative 3-D Serial Growth Pattern Studies of Oral-Facial Structures," AADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging q Applications for Automated Industrial Inspection and Assembly, vol. 182, p. 187-191 (1979).

Altschuler, "3D Mapping of Maxillo-Facial Prosthesis," AADR Abstract #607, 2 pages total, (1980).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A ProgressReport," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff et al., "Computerized Analysis of Occlusion in the Postcanine Dentition," Am. J. Orthod., 61(3): 245-254 (Mar. 1972).

Biggerstaff, "Computerized Diagnostic Setups and Simulations," Angle Orthod., 40(1):28-36 (Jan. 1970).

Biostar Opeation & Training Manual. Great Lakes Orthodontics, Ltd. 199 Fire Tower Drive,Tonawanda, New York. 14150-5890, 20 pages total (1990).

Blu, et al., "Linear interpolation revitalized", IEEE Trans. Image Proc., 13(5):710-719 (May 2004).

Bourke, "Coordinate System Transformation," (Jun. 1996), p. 1, retrieved from the Internet Nov. 5, 2004, URL <http://astronomy.swin.edu.au/—pbourke/prolection/coords>.

Boyd et al., "Three Dimensional Diagnosis and Orthodontic Treatment of Complex Malocclusions With the Invisalipn Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: Comparison with Manual Measurements of Mesio-distal Diameter," J. Dent. Res., 65(3):428-431 (Mar. 1986).

Burstone (interview), "Dr. Charles J. Burstone on the Uses of the Computer in Orthodontic Practice (Part 1)," J. Clin. Orthod., 13(7):442-453 (Jul. 1979).

Burstone (interview), "Dr. Charles J. Burstone on the Uses of the Computer in Orthodontic Practice (Part 2)," J. Clin. Orthod., 13(8):539-551 (Aug. 1979).

(56) References Cited

OTHER PUBLICATIONS

Burstone et al., Precision Adjustment of the Transpalatal Lingual Arch: Computer Arch Form Predetermination, Am, Journal of Orthodontics, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk to the Operatory, Canadian Dental Journal, vol. 54(9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin Orthod., 7(4):258-265 (Dec. 2001).
Cutting et al., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production, pp. 1-7 (Jan. 1992.
Definition for gingiva. Dictionary.com p. 1-3. Retrieved from the internet Nov. 5, 2004 <http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium on Computer Restorations: State of the Art of the CEREC-Method, May 1991, 2 pages total.
Dentrac Corporation, Dentrac document, pp. 4-13 (1992).
Dent-X posted on Sep. 24, 1998 at <http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances-Pro Lab, 1 page (1997).
Duret et al, "CAD-CAM in Dentistry," J. Am. Dent. Assoc. 117:715-720 (Nov. 1988).
Duret et al., "CAD/CAM Imaging in Dentistry," Curr. Opin. Dent., 1:150-154 (1991).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet: <http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
GIM-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management, "J. Clin. Orthod., 16(6):390-407 (Jun. 1982).
Grayson, "New Methods for Three Dimensional Analysis of Craniofacial Deformity, Symposium: Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Heaven et al. "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), lnformatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances-Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling et al., The Philosophy of the Tooth Positioning Appliance, American Journal of Orthodontics and Oral surgery. 1945; 31:297-304.

(56) References Cited

OTHER PUBLICATIONS

Kesling, Coordinating the Predetermined Pattern and Tooth Positioner with Conventional Treatment, Am. J. Orthod. Oral Surg. (1946) 32:285-293.
Kleeman et al., The Speed Positioner, J. Clin. Orthod. (1996) 30:673-680.
Kochanek, "Interpolating Splines with Local Tension, Continuity and Bias Control," Computer Graphics, 18(3):33-41 (Jul. 1984).
Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy as One, Two, Three," AOA/Pro Corner, vol. 11, No. 1, 2 pages (2002).
Mormann et al., "Marginale Adaptation von adhasuven Porzellaninlays in vitro," Separatdruck aus:Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
Procera Research Projects, "Procera Research Projects 1993—Abstract Collection," pp. 3-7 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and Essix Appliances, <http://www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow et al. "CAD/CAM for Dental Restorations—Some of the Curious Challenges," IEEE Trans. Biomed. Eng., 38(4):314-318 (Apr. 1991).

Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Surg., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively).
Shilliday, (1971). Minimizing finishing problems with the minipositioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee Orthodontic Appliances-Pro Lab product information for doctors. http://ormco.com/aoa/appliances-services/RWB/doctorhtml>, 5 pages (May 19, 2003).
The Choice is Clear: Red, White & Blue . . . The Simple, Affordable, No-Braces Treatment, Allesee Orthodontic Appliances-Pro Lab product information for patients, <http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile! Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).

(56) References Cited

OTHER PUBLICATIONS

U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); Ill.—The General Concept of the D.P. Method and Its Therapeutic Effect, Part 2. Skeletal Reversed Occlusion Case Reports," Nippon Dental Review, 458:112-129 (Dec. 1980).
Yoshii, "Research on a New Orthodontic Appliance: The Dynamic Positioner (D.P.); Ill. The General Concept of the D.P. Method and Its Therapeutic Effect, Part 1, Dental and Functional Reversed Occlusion Case Reports," Nippon Dental Review, 457:146-164 (Nov. 1980).
You May Be a Candidate for This Invisible No-Braces Treatment, Allesee Orthodontic Appliances-Pro Lab product information for patients, 2 pages (2002).

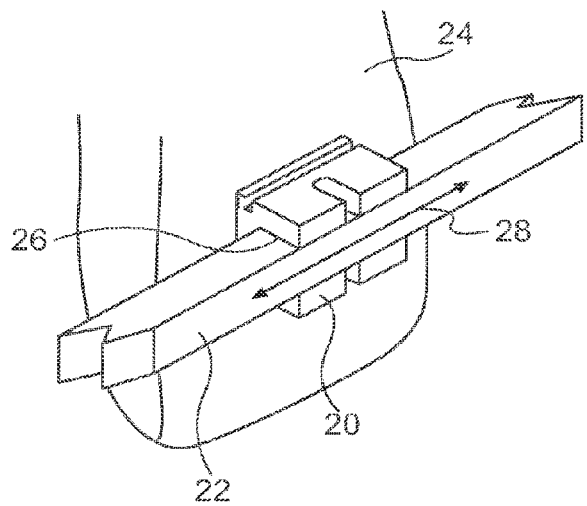
FIG. 1
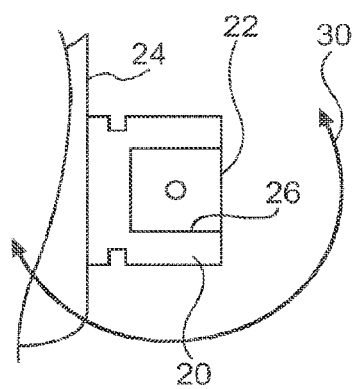
FIG. 2
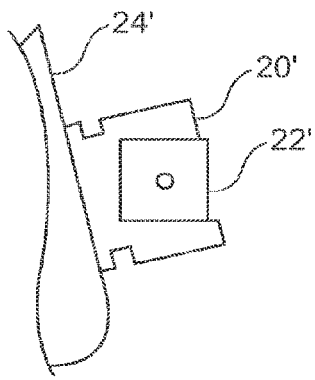
FIG. 3
| | BAND | BRACKET | WIRE | VECTOR |
|---|---|---|---|---|
| TOOTH | | | | |
UR ☐ ☐ ☐ ☐ ☐   ☐ ☐ ☐ ☐ ☐ UL
    5 4 3 2 1   1 2 3 4 5
LR ☐ ☐ ☐ ☐ ☐   ☐ ☐ ☐ ☐ ☐ LL
| OPEN | |
|---|---|
FIG. 4

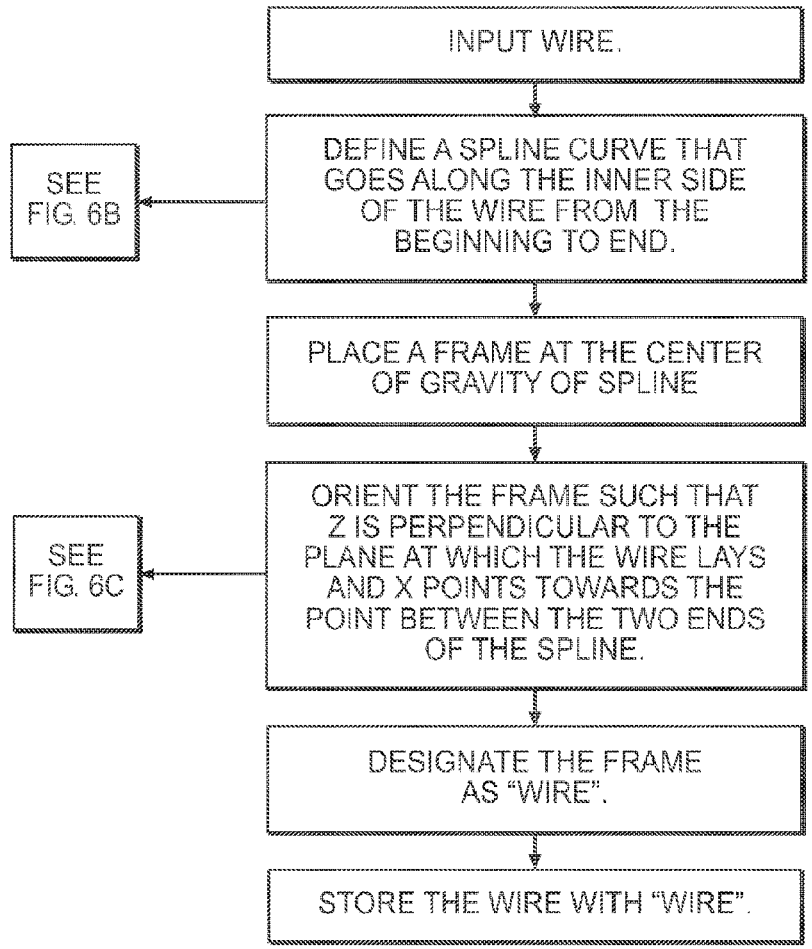
*FIG. 6A*
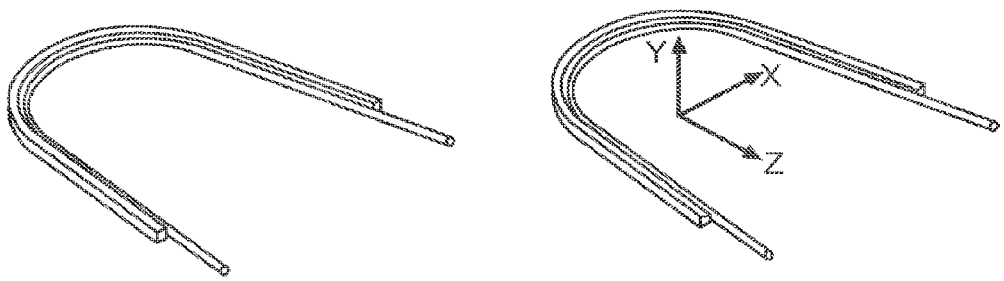
*FIG. 6B*     *FIG. 6C*

VIRTUAL ORTHODONTIC TREATMENT

CROSS-REFERENCE

This application is a continuation of U.S. patent application Ser. No. 12/967,347, filed Dec. 14, 2010, now U.S. Pat. No. 9,375,293, issued Jun. 28, 2016, which is a continuation of U.S. patent application Ser. No. 11/889,111, filed Aug. 9, 2007, now U.S. Pat. No. 7,866,978, issued Jan. 11, 2011, which is a continuation of U.S. patent application Ser. No. 10/749,388, filed Jan. 2, 2004, now U.S. Pat. No. 7,275,930, issued Oct. 2, 2007, which is a continuation of U.S. patent application Ser. No. 09/591,757, filed Jun. 12, 2000, now U.S. Pat. No. 6,739,869, issued May 25, 2004, which is a continuation of International Application No. PCT/IL1998/000593, filed Dec. 7, 1998, which claims priority to Israeli Patent Application No. 122807, filed Dec. 30, 1997, the entire contents of each of which are hereby incorporated by reference.

FIELD AND BACKGROUND OF INVENTION

The present invention is generally in the field of orthodontics.

An orthodontic treatment has the objects of moving and reorienting teeth for both functional or aesthetic purposes. In such a treatment, the orthodont places a variety of orthodontic components on the teeth including brackets, which are firmly fixed to the teeth, and other components including wires, tensioning springs, etc., which apply forces and moments on the teeth, through the brackets, thereby causing the teeth to move. A major problem facing the orthodont is to predict the final outcome of the orthodontic treatment. Another problem to focus is to define the proper placement of the brackets and to select the proper force-inducing components to best yield the desired outcome. Currently, the design and predicting of orthodontic treatment is based mainly on the orthodonts personal "look and feel" and prior experience skills. This approach is not only error prone but also varies from one individual to the other, which is obviously undesired.

There is accordingly a need in the art to provide the orthodont with a tool for visual demonstration, design or predicting of possible outcome of an orthodontic treatment. Provided by the invention are method and system therefor.

GENERAL DESCRIPTION OF THE INVENTION

In the context of the present description and the appended claims, the term "movement" or "moving" refers to repositioning teeth, reorientating teeth, or both. The term "orthodontic treatment" refers to a treatment intended to move at least one tooth; namely, an orthodontic treatment should be understood as encompassing a procedure where all or only part of the teeth (e.g. teeth of one jaw, a group of teeth in a section of a jaw, etc.) are moved. Furthermore, the term "orthodontic treatment" refers both to a treatment intended to yield movement to reach a final, close to ideal outcome of the treatment as well as to an interim treatment yielding an interim position and orientation of the teeth. In other words, the term "orthodontic treatment" mentioned herein encompasses both a treatment from an initial stage, i.e. before the treatment began, through to a final stage; a treatment from an initial stage to an interim stage; as well as to a treatment from an interim stage to another interim or final stage.

The term "virtual treatment" (referred to also, occasionally as virtual orthodontic treatment) as used herein means an orthodontic treatment as simulated on a computer. A virtual treatment may use virtual components (i.e. 'component' in the virtual computer environment) such as brackets, wires, tensioning springs or rubber bands, corresponding to real components as used in a real life orthodontic treatment, but may also use components which are not normally used in real-life treatment; and also components used in real-life treatment but are used in the virtual treatment in a different manner. Thus, for example, a virtual orthodontic treatment may use wires which are not normally used in a real life orthodontic treatment; may use wires of a cross-section other than such used in a real-life orthodontic treatment; may combine wires and brackets in a manner whereby the brackets are biased towards a rotational movement around the axis of the wire which is usually not performed in a real-life orthodontic treatment; etc. It will therefore be understood that the result of virtual treatment is not necessarily the same as the actual real treatment.

In the following, a method and system for virtual treatment is disclosed. Manual systems may be used by an orthodont to examine various alternative treatment paradigms and compare them to one another so as to see which one will yield the best result. For example, the orthodont may compare a treatment where one or more teeth are extracted to another treatment where all teeth are left in tact. In addition, the system and method of the invention may allow also the orthodont to select the orthodontic components which he will eventually use in the real-life treatment, to predict the course, time and cost of the treatment. This will all be clarified from the disclosure below.

It will also become clear from the following disclosure, the orthodontic treatment may be made to resemble a real-life orthodontic treatment, although not necessarily so, and occasionally, the orthodontic treatment may use components or may apply a set of rules which are not directly applicable to real-life treatment.

The present invention provides, by one of its aspects, a method for virtual orthodontic treatment, comprising:

(a) providing a first virtual three-dimensional image indicative of a three-dimensional (3D) model of teeth from at least one jaw, the model being manipulable so as to allow its viewing from a desired direction;

(b) selecting a virtual set of orthodontic components, and associating the components with the teeth of said first image so as to obtain a second image of said 3D model with said components associated therewith;

(c) using a set of rules, including at least one rule, defining the effect of said set of components on said teeth, computing the manner of movement of the teeth as a result of said effect, so as to obtain a third image comprising the teeth model following the virtual treatment.

The set of orthodontic components selected in step (b) includes components which are capable of imparting movement between at least two teeth. For example, the set may include at least two brackets and a wire, may include rubber bands or tensioning springs for forcing two teeth one against the other, etc. Typically, the set of orthodontic components includes for each jaw, typically, but not necessarily, about 5 to about 10 brackets in the case of a child's jaw, and between about 5 to about 16 in the case of an adult's jaw.

The set of orthodontic components may be represented as an image which is similar to the image of the real orthodontic component, as seen in real life. However, orthodontic component may also be represented by any other graphic representations. For example, the wire may be represented by a straight or curved line; a bracket may be represented by a rectangular frame, etc.

In accordance with some embodiments of the invention, the set of components includes brackets and a wire and the rule dictates that eventually all slots which receive the wire will be aligned with the wire where the latter is arranged as a splined curve indicative of the desired result of the virtual treatment. In other words, in this case the wire represents the desired results of alignment of all slots following the virtual treatment. Thus, by such an embodiment a component which represents a real-life component, i.e. a wire, is used in a different manner than in a real-life treatment in that it dictates the result of the treatment. This embodiment thus illustrates a general principle in some embodiments of the invention that while in a real-life treatment components act in combination to apply forces on teeth and the movement is a result of such applied forces, in a virtual treatment of the invention, the components may also dictate the final result. However, this does not exclude a possibility, in accordance with some other embodiments of the invention, where the movement of the teeth is dictated by forces and moments, which in this case are the set of rules, which act on the teeth under influence of the different components.

Thus, as will be appreciated, occasionally, the component and the set of rules may be associated with one another. Taking the previously illustrated embodiment as an example, the component, which is a wire defining a splined curve, has with it an associated rule dictating that the brackets, with the associated teeth, should move, vertically, but possibly also horizontally, so that all brackets will eventually be positioned such that their respective slots are on the splined curve defined by the wire. In addition to the desired final result, the set of rules may also stipulate the computational algorithm defining the manner of movement of the teeth to yield said final result.

The set of rules may also allow, for example, the removal of the tooth in certain circumstances. For example, in the case of crowdness, i.e. insufficient space for all teeth to assume an ideal position and orientation (a position and orientation such that the apex of all teeth are essentially on one splined curve), an interfering tooth may be removed. The removal may, by one embodiment, be automatic; by another embodiment, the user may decide in such a case which tooth is to be removed.

As will be explained in greater detail below, the set of rules is not limited to a specific implementation. Thus, by way of example, the set of rules may be extracted from a static set of rule database, or by way of another example from a dynamic learning database holding a rule base that may be adjusted depending upon e.g. various characteristics of the individual patient that undergoes the treatment.

The purpose of the virtual orthodontic treatment may be to change the relative orientation of the teeth, to change a distance between the teeth, to alter the inter-occlusion of distance between teeth of opposite jaws, etc.

In accordance with one example, where the teeth are such that they do not fill the entire space in a jaw (namely with an edge of one tooth being in proximity to a neighbouring tooth), the set of rules may also allow the addition of a tooth, which may, in the case of a child's jaw, represent a tooth which has not yet grown or, in the case of an adult's jaw, a crown which may be implanted in a real-life treatment.

Steps (b) and (c) may be repeated a plurality of times until obtaining a desired result of the virtual treatment. In a repeated step (b), a component already selected in a previous step may associated with the teeth model in a different manner, e.g. applying it on a different tooth, orienting it on a tooth in a different manner, etc.; or new components may be selected, e.g. new brackets, new rubber bands, a different wire; etc.

The 3D teeth model may, be of all teeth in a jaw, may be a model of teeth of both jaws, may be a model of part of the teeth of one or both jaws.

The term "associating" as used herein denotes the entire range of combining orthodontic components with teeth and to typically (but not necessarily) in a manner that stimulates combination thereof in real life treatment. Typical, but not exclusive examples, being: attaching brackets to teeth at different positions or orientations; fixing a wire into the bracket's wire-receiving slot; sliding the bracket and the wire one with respect to another, changing the angle of the wire-receiving slot within the bracket so as to change the torque or moment between the wire and the bracket; fixing a tensioning spring or band around two adjacent, teeth; etc. The wire chosen within the framework of the virtual treatment may have various geometries, e.g. straight or spline-curved, and various cross-sectional shapes, e.g. circular, oval, rectangular, etc. (usually to track the ideal curvature of the teeth arrangement in a jaw).

In accordance with another aspect of the invention, there is provided a method for designing orthodontic treatment of teeth from at least one jaw, comprising:

(a) providing a virtual three-dimensional image indicative of a three-dimensional model of the teeth in a manner allowing manipulation of the model for viewing the model from a desired direction;

(b) selecting a virtual set of orthodontic components corresponding to those intended to be used in said orthodontic treatment and associating the components with the teeth of said first image so as to obtain a second image of said three-dimensional model with said components associated therewith in a manner representing the manner in which said components and the teeth may combined in said orthodontic treatment;

(c) using a set of rules, including at least one rule, defining the manner in which said components affect movement of the teeth, so as to obtain a third image comprising the teeth model after movement of the teeth affected by said components;

(d) repeating steps (a) and (c) until a desired third image is obtained, which desired third image represents a desired position and orientation of teeth following the orthodontic treatment;

(e) recording said second image which yields, following step (c), the desired third image and using it as a basis for designing the orthodontic treatment.

In addition to allowing a design of the treatment, the method in accordance with the second aspect may also be used to predict the length of the treatment as well as its costs.

By a further aspect the present invention provides a system for a virtual orthodontic treatment, comprising:

(a) storage means capable of storing a first virtual three-dimensional image indicative of a three-dimensional model of teeth of at least one, substantially entire jaw;

(b) user interface for enabling selection of a virtual set of orthodontic components;

(c) processor capable of at least:

(c1) manipulating said three-dimensional model to allow its viewing from a desired direction, (c2) associating said set with the teeth of said first image to obtain a third image of said three-dimensional model with said components associated therewith, and (c3) applying a set of rules, including at least one rule, determining effect of said components on the teeth so as to cause virtual movement of the teeth as a result of association with said components to obtain a third teeth model; and (d) display means for displaying the images.

Regardless of the aspect under consideration, the generation of virtual three-dimensional image may be obtained, e.g by following the technique described in PCT Publication No. WO 97/03622, the contents of which is incorporated herein by reference.

By a still further aspect the present invention provides an apparatus having a memory which contains a digital image representing a three-dimensional teeth model following a virtual orthodontic treatment, which image was generated by any of the above methods.

By a further aspect there is provided a memory for storing data for access by an application program, implementing the steps (b)-(c) according to a method of each of the above aspects; the application program being executed on a data processing system; the data representing a first virtual three-dimensional image, indicative of the three-dimensional model of teeth of one jaw. Also provided is a memory for storing data representing a second virtual three-dimensional image, obtained by implementing the above method.

BRIEF DESCRIPTION OF THE DRAWINGS

For a better understanding, the invention will now be described by way of example only with reference to the annexed drawings in which:

FIG. 1 illustrates two components, a bracket and a wire, selectable by the user in a virtual treatment in accordance with one embodiment of the invention;

FIG. 2 is a cross-sectional view along line I-I in FIG. 2;

FIG. 3 is the same cross-sectional view as in FIG. 2, after change in the slot angle;

FIG. 4 illustrates one view of user interface, according to an embodiment of the invention;

FIG. 6A is a block diagram illustrating the manner of defiling a wire for use within the framework of a virtual treatment in accordance with an embodiment of the invention;

FIG. 6B and FIG. 6C illustrate the manner in which the wire is viewed in various steps of the process of FIG. 6A;

DETAILED DESCRIPTION OF THE INVENTION

Figure 5A:
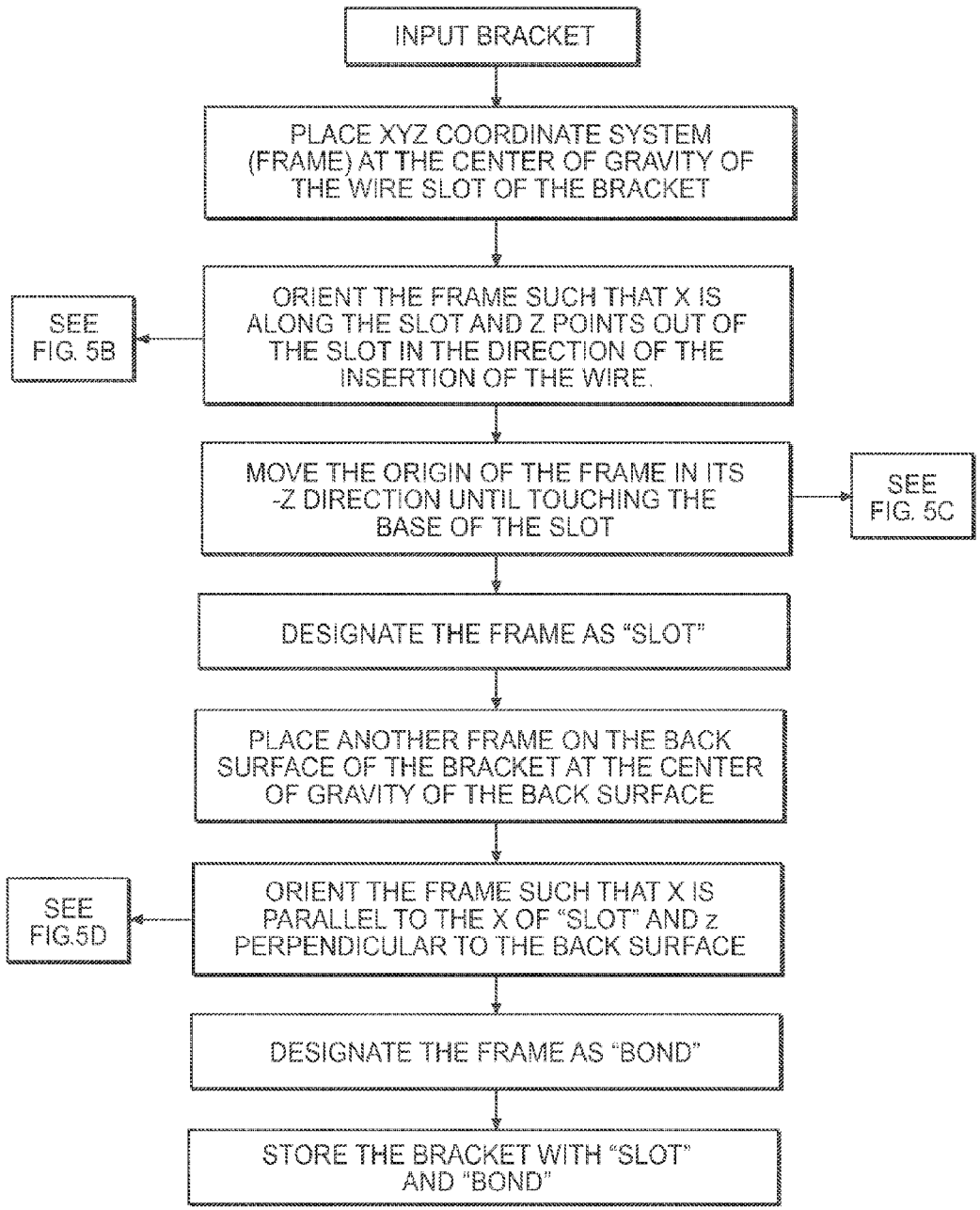
FIG. 5A is a block diagram illustrating the manner of defining a brackets for use in the framework of virtual treatment in accordance with an embodiment of the invention.

The present invention provides a method and system for virtual movement of teeth using the framework or a set of rules from which is based in real life, although not necessarily identical.

In the following, the invention may at times be described with a reference made to various physical entities, such as "jaw", "bracket", "wire", "band", etc. It should, however, be understood that it implies, in most cases, to a representation of these entities that is used in the virtual treatment. There are some exceptions where reference is made to real physical objects, which fact may clearly be inferred based on the context.

Teeth movement in a virtual, computerized 3D environment for the purpose of planning an orthodontic treatment or for any other purpose, is a complicated task if this is being performed using hitherto known techniques. The use of techniques known to the orthodont from a real orthodontic treatment, simplifies this virtual orthodontic treatment.

The virtual treatment may be required, at times, to allow the orthodont to determine a potential outcome of orthodontic treatment. For such a purpose, the virtual treatment need not necessarily follow a course to be followed by the real orthodontic treatment since the focus may be only on the final outcome, namely on the final position and orientation of the teeth following the treatment. In such a treatment, the orthodont may utilize orthodontic components and combination between such components, even such not used in real life orthodontic treatment. Examples are a selection of a wire with a different geometry than that used in real life or, change hi the slot angle within the brackets so as to yield an angular moment on the teeth about the axis of the wire (see FIG. 3).

If, however, a virtual treatment is intended to simulate the real treatment for the purpose of treatment design, preferably (but not necessarily), only orthodontic components which simulate those used in real life orthodontic treatment, will be used.

In a typical yet not exclusive sequence of operation in virtual treatment, the user first selects brackets and places them at appropriate positions on the surface of selected teeth, usually all teeth of the jaw. In most cases brackets are placed on the buckal teeth surface; however, occasionally, in the virtual treatment brackets may alternatively or additionally be placed on lingual surfaces of the teeth (this may also be followed at times in real life orthodontic treatment).

At a next step, the user may define the final desired distance between the teeth (the default is usually zero) and then selects an arch-wire from a library of such wires. The library may include wires of different widths, different cross-sectional shapes, and different geometries. Optionally, it is possible also to change the geometry of the selected wire, e.g. to make it to follow a tortous path in a vertical and/or a horizontal plane, etc.

Thereafter, the wire may be associated with the teeth model, for example, by combining them with virtual-brackets fitted on the teeth surface or by attaching them first to virtual anchoring molars, and then to virtual brackets, etc. The effect of the components on each tooth is thereafter computed by the system, based on the set of rules to determine the outcome of the virtual treatment.

If the virtual treatment uses components which simulate real-life components, once an optimal result of virtual treatment is reached, the parameters, namely the type of components which were used and the mariner they were combined with one another and with the teeth model, may be recorded and this may then used to generate a prescription for the orthodontic treatment. Such a prescription may specify the type of components used, the exact position of each component, e.g. the position of the bracket on each tooth, etc.

The virtual treatment may obviously also provide a tool to estimate the treatment length and costs.

The invention will now be further illustrated with reference to some specific, non-limiting embodiments, with reference to the annexed drawings.

FIGS. 1-3 show examples of a set of components which can be used in accordance with an embodiment of the invention. In this specific embodiment, the components consist of a bracket 20 and wire 22 fixed on a surface of a tooth 24, of which only a portion thereof represented by a rectangle is seen. The user has freedom of choice of the exact position of attachment of the bracket 20 on the surface of the tooth 24 and also can slide wire 20 in a longitudinal axis within the receiving slot 26 of the bracket, as represented by the bi-directional arrow 28.

The wire and the bracket may be associated with one another in different relative orientations. In the example shown in FIGS. 1 and 2, the wire, which in this case has a rectangular cross-section, is received in a slot with walls parallel and normal to the tooth's surface. By some embodiments of the invention it is possible to change the angle of slot 26 about its central axis, as represented by arrow 30, in FIG. 2 to yield a state such as that shown in FIG. 3, wherein wire 22' has a different angular orientation, with respect to bracket 20', thereby applying a moment onto tooth 24'.

FIG. 4 shows an example of an embodiment of one out of many possible variants of a user interface for realizing the initial component selection steps. The user can select the brackets from a library of brackets, and similarly can select wires, bands etc. from corresponding libraries. In addition, the user has the ability to determine the type of forces and their direction which will act on each tooth.

Figure 5B:
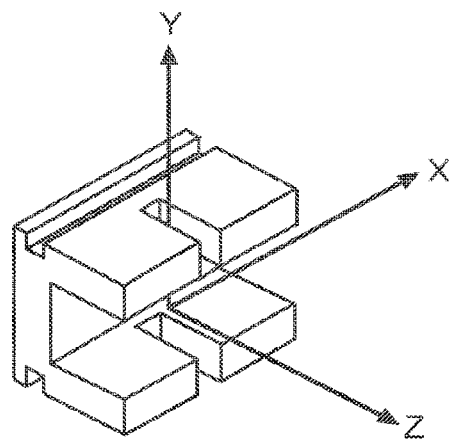
FIGS. 5B-5D illustrate the brackets as viewed in various steps of the selection process.
Figure 5C:
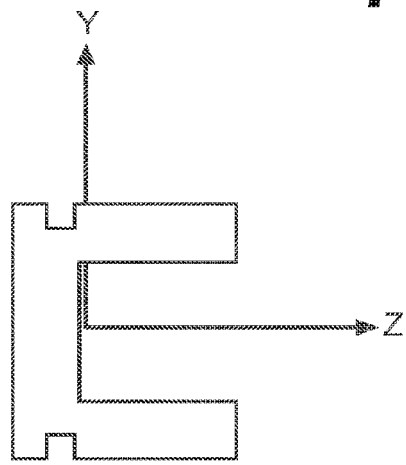
Figure 5D:
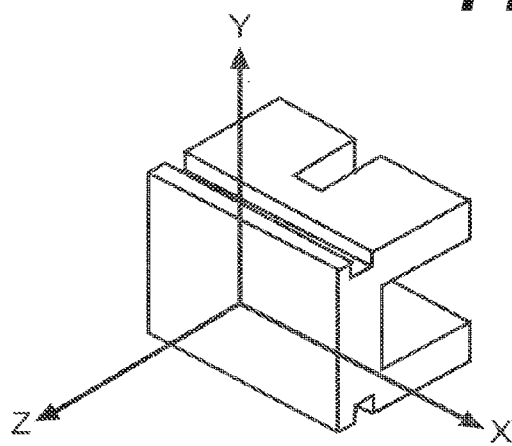

FIG. 5A illustrates, the manner of defining a bracket for use in subsequent virtual treatment steps. In this process, the bracket is defined with respect to a relative; coordinate system to allow its subsequent association with the wire, thus defining a "SLOT" frame of reference; (illustrated graphically in FIGS. 5B and 5C) as well as to define another coordinate system to facilitate attachment of the bracket to the teeth, thus defining the "BOND" reference frame (illustrated graphically in FIG. 5D).

Although the steps of bracket definition are typically carried once, while creating the bracket library, it may also be repeated prior to each virtual treatment step while selecting brackets for the treatment.

FIG. 6A illustrates the steps of choosing a wire and defining it such that it can be subsequently used in the framework of virtual treatment. A wire is selected, its initial curve is defined (illustrated graphically in FIG. 6B) and then the wire is placed in a relative coordinate system (illustrated graphically in FIG. 6C), so as to define a "WIRE" frame of reference, for subsequent use. Obviously, as will be appreciated, the x-y-z coordinate system of the "WIRE" frame of reference should correspond to the x-y-z coordinate system of the "SLOT" reference frame.

Figure 7:
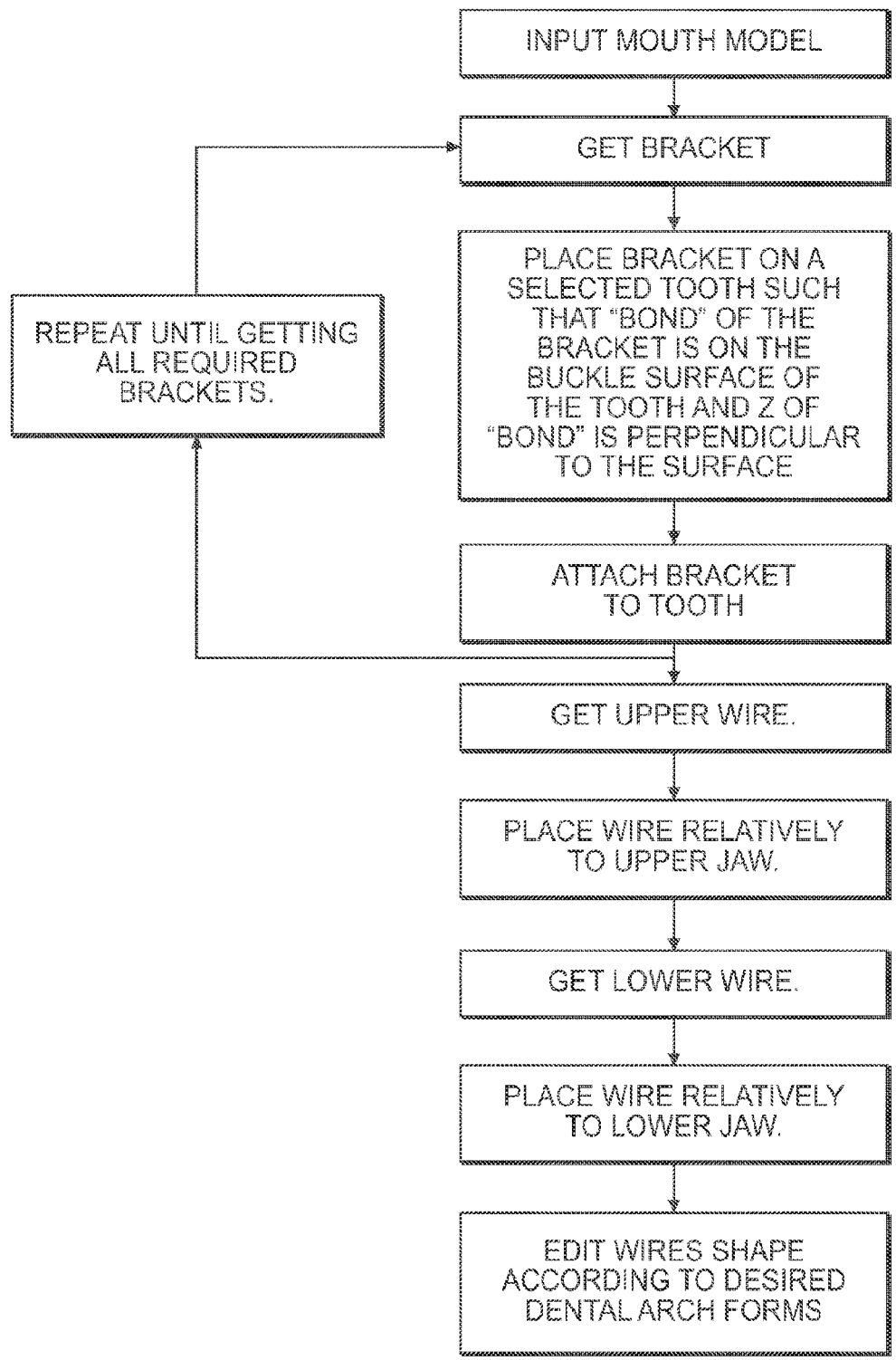
FIG. 7 is a block diagram illustrating the manner of attaching the brackets onto teeth in the virtual treatment, in accordance with an embodiment of the invention.

FIG. 7 illustrates the steps of attachment of a bracket onto a tooth. A teeth model is acquired, brackets are selected from the library and each bracket is placed on a tooth using the "BOND" reference frame, such that the z axis of the BOND frame of reference is perpendicular to the surface. Once the bracket is placed at the desired location, it is both fixed in this location and then the process is repeated a plurality of times in accordance with the number of brackets to be placed on the teeth.

Figure 8:
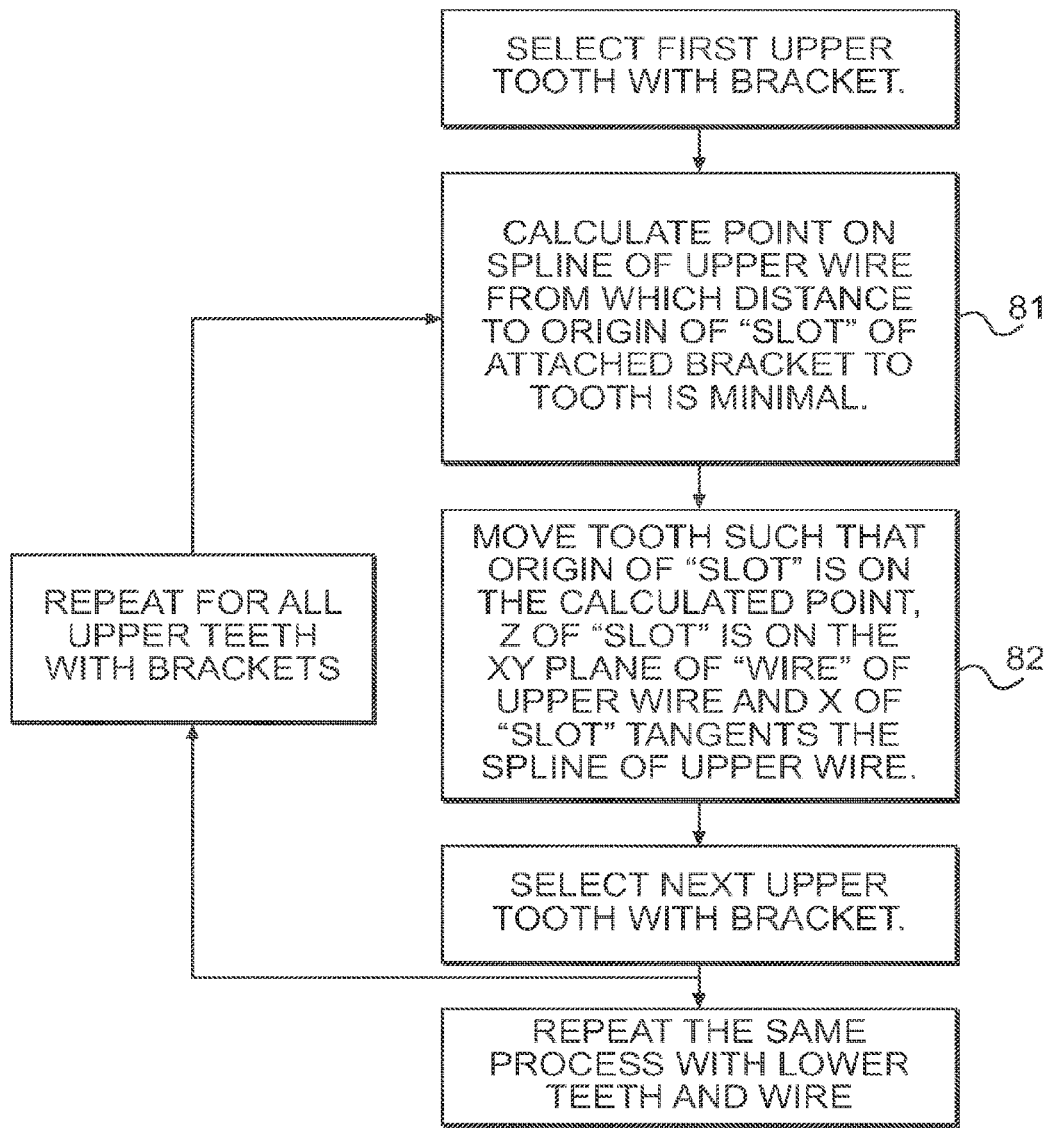
FIG. 8 is a block diagram illustrating the steps of matching wires to jaws and vertical movement of teeth to a position dictated by the wire.

FIG. 8 illustrates the steps of matching the wires to the jaws. The wires are selected from a library, and placed so that their spline curve will match that of the jaw or their spline curve may at times be edited to amend it in accordance with the particulars' parameters of the jaw in a particular teeth model. In the specific Example shown, the process is first performed for the upper jaw and then for the lower jaw, although it will be appreciated that this sequence may be altered, e.g. reversed, performed intermittently in the upper and lower jaws, etc.

In this specific embodiment, the orientation and position of the wire dictates the final result, i.e. final alignment of all slots in the bracket. In other words, in this specific embodiment a set of rules applied in the virtual treatment includes, at minimum, a requirement for vertical realignment of the slots, and hence of the teeth to which they are attached, so that all slots will arrive to the wire. The set of rules also dictate how to accomplish this result. Put differently, as a result of the virtual treatment, in the final orientation which will be accomplished in the resulting teeth model, the wire will remain at the same position and the teeth displaced such that the wire snaps into the slots of the bracket. This procedure is illustrated in FIG. 8, where the set of rules is dictated in blocks 81 and 82.

Figure 9:
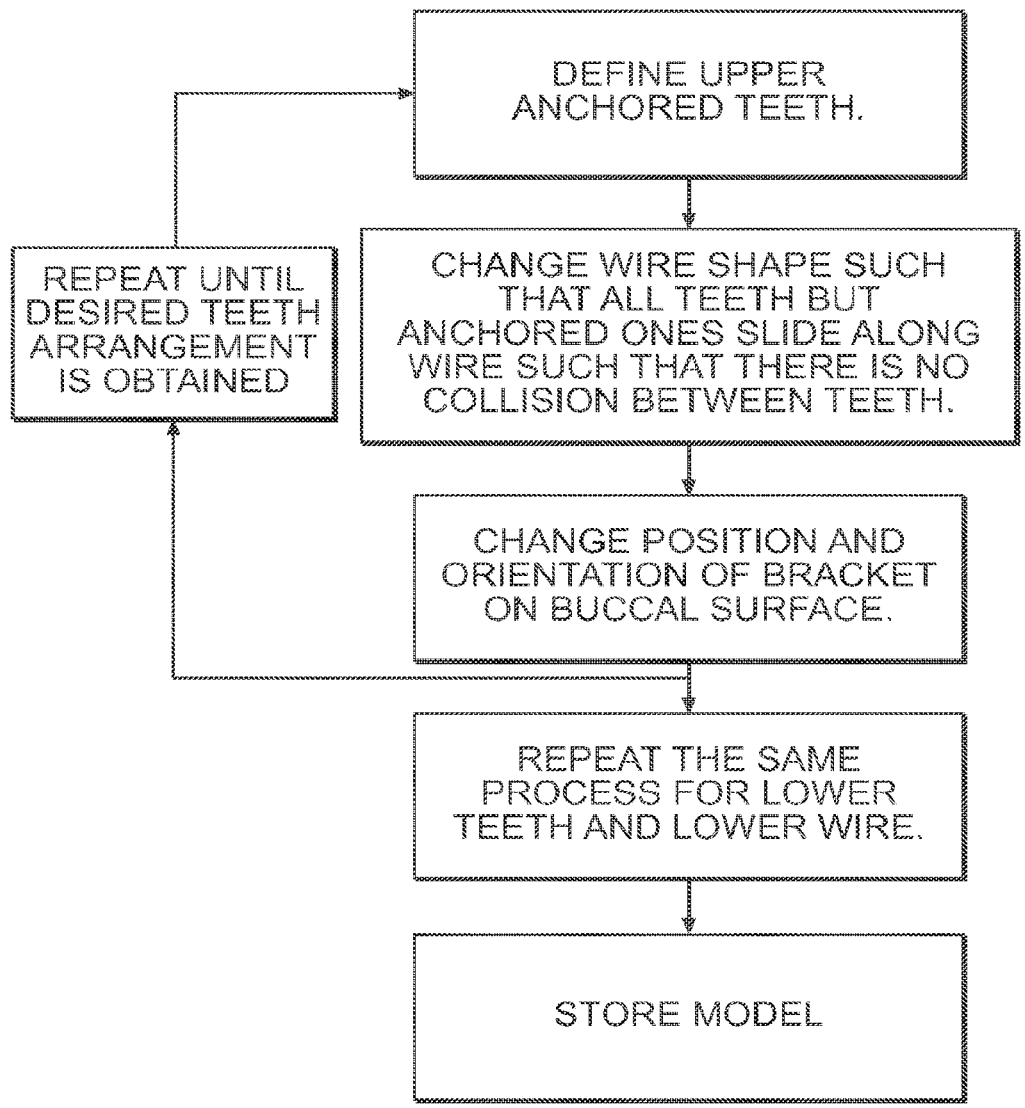
FIG. 9 is a block diagram illustrating the steps of horizontal movement of teeth in the case of crowdness, i.e. collision between teeth.

Another set of rules which can be applied in case of collision between the teeth, i.e. in case of crowdness. This is illustrated in FIG. 9 where the teeth are moved horizontally by sliding along the wire, to avoid such collision. The manner in which the virtual treatment is performed may allow also some user intervention. For example, the user can define some teeth which may have to remain stationary, and others which are allowed to move. Alternatively, the system may have a wider degree of freedom, to allow sideways movement of all teeth. As also illustrated in FIG. 9, it is possible in this process to provide the user with an additional degree of freedom, which involves changing the position and/or orientation of the bracket on the tooth surface.

Figure 10A:
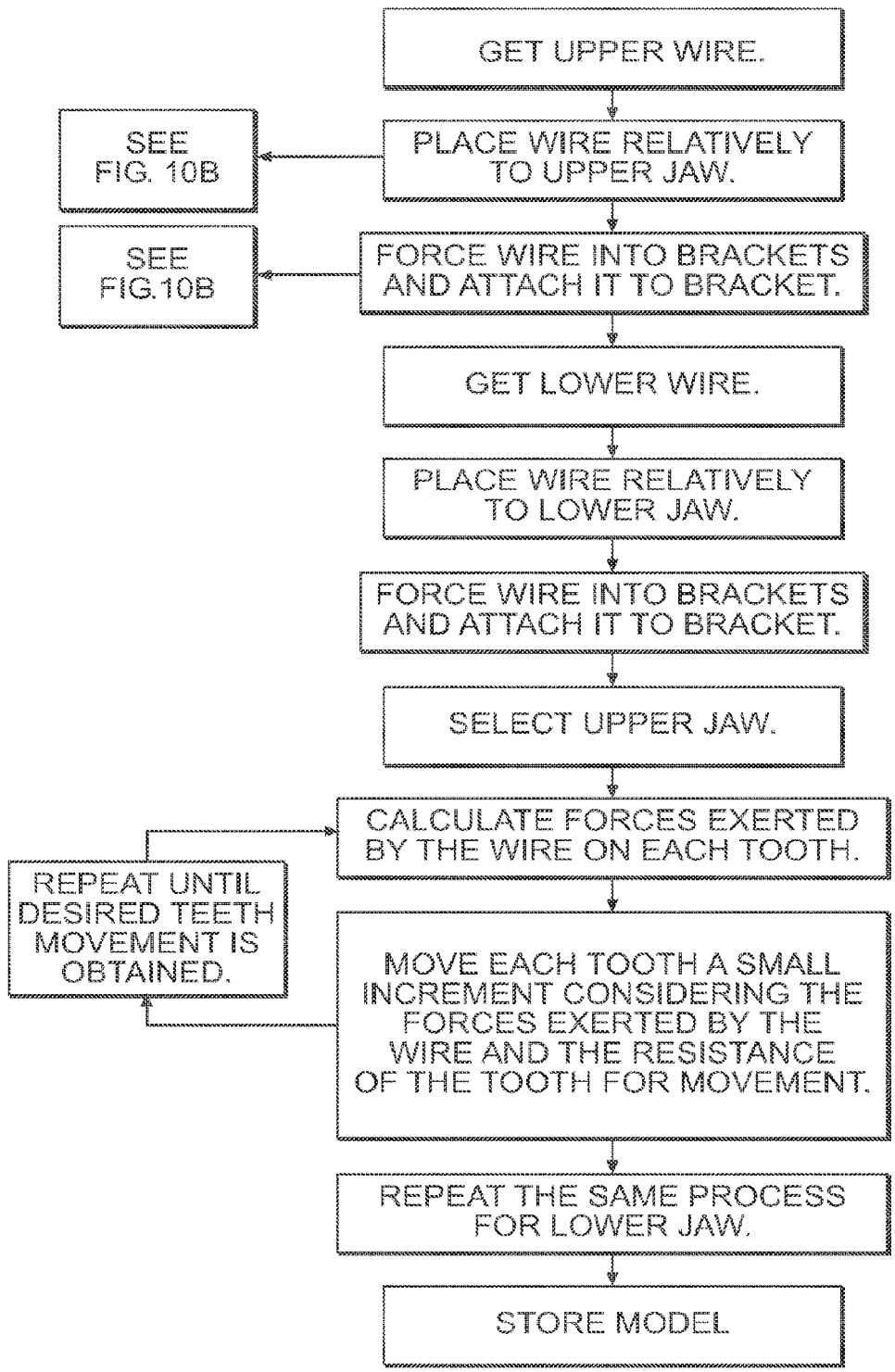
FIG. 10A is a block diagram illustrating the steps of matching wires to a jaw, in accordance with another embodiment of the invention, and movement of teeth as a result of virtual forces exerted by the wire or the teeth.
Figure 10B:
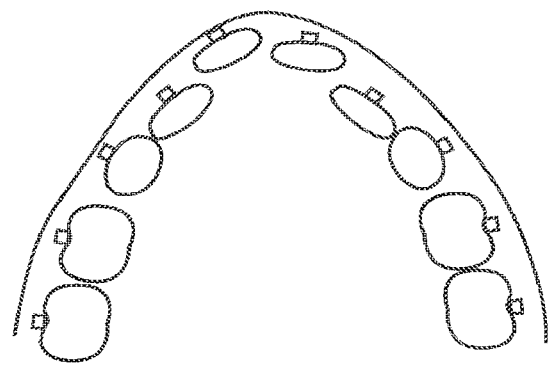
FIGS. 10B and 10C illustrate the manner in which the association between the wire and the teeth is viewed in two steps of the process of FIG. 10A.
Figure 10C:
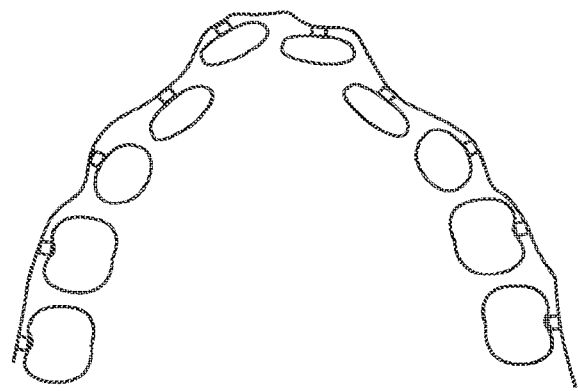

FIG. 10 illustrates another embodiment of teeth movement within the framework of a virtual treatment of the invention. As illustrated in FIG. 10A, wires are obtained, positioned in proximity of the jaw (illustrated graphically for the upper jaw in FIG. 10B), its shape edited so as to attach to the brackets on the teeth (illustrated graphically in FIG. 10C) and then the forces applied by the wire on the teeth are calculated and the final position of the teeth obtained can then be stored.

The present invention has been described with a certain degree of particularity but it should be understood that various modifications and alterations may be made without departing from the scope or spirit of the invention as defined by the following claims:

What is claimed is:

1. A method for virtual orthodontic treatment using a computer system, comprising:
   (a) providing a first virtual three-dimensional (3D) image indicative of a 3D model of all teeth of at least one jaw;
   (b) selecting a virtual set of orthodontic components, comprising (i) brackets, one for each tooth in said first virtual three-dimensional (3D) image, for attachment to teeth of said first virtual three-dimensional (3D) image, each of said brackets having a slot for engaging a wire, and (ii) one or two archwires;
   (c) associating the brackets with the teeth of said first virtual three-dimensional (3D) image so to obtain a second image of said virtual 3D model with the brackets associated with the teeth of the model, one bracket on each tooth in said model;

(d) using a set of rules, including a rule that requires each slot to engage the archwire, computing the manner of movement of each tooth with the bracket associated therewith, so as to obtain a third image comprising the teeth model following the virtual treatment;

(e) changing at least one bracket or the manner of associating a bracket with a tooth and repeating steps (c) and (d) one or more times until the teeth model of said third image represents a desired outcome of the orthodontic treatment; and (f) outputting at least the third image from the computer system.

2. The method according to claim 1, further comprising providing a user interface and wherein said selecting comprises using the user interface for selecting the virtual set of orthodontic components.

3. The method according to claim 1, wherein said associating comprises manually associating the selected brackets with the teeth of said first virtual three-dimensional (3D) image.

4. The method according to claim 1, wherein said associating comprises automatically associating the selected brackets with the teeth of said first virtual three-dimensional (3D) image.

5. The method according to claim 1, wherein said first virtual three-dimensional (3D) image is a virtual representation of a three-dimensional (3D) model of the individual's teeth at interim treatment stage and said third image is a virtual representation of an interim or a final treatment stage.

6. The method according to claim 1, wherein the virtual orthodontic components are represented by an image which is similar to the image of a real life component.

7. The method according to claim 1, wherein the virtual orthodontic components are represented graphically in a manner not resembling the image of a real life component.

8. The method according to claim 1, wherein said set of rules is extracted from a dynamic learning database holding an adjustable rule base.

9. The method according to claim 8, wherein the adjustment of the database is based on characteristics of the individual undergoing the orthodontic treatment.

10. The method according to claim 1, comprising virtually extracting one or more teeth from the teeth model of said first virtual three-dimensional (3D) image.

11. The method according to claim 10, wherein said set of rules includes a rule that defines movement of teeth to occupy space previously occupied by an extracted tooth.

12. The method according to claim 10, wherein the virtually extracting is performed manually by a user.

13. The method according to claim 10, wherein the virtually extracting is performed automatically in case of teeth crowdedness.

14. The method according to claim 1, comprising virtually adding a tooth to the model of said first virtual three-dimensional (3D) image.

15. The method according to claim 14, wherein the added tooth represents one that has not yet grown.

16. The method according to claim 14, wherein the added tooth represents a crown that may be added or implanted in a real-life treatment.

17. The method according to claim 1, wherein at least one of said repetitions of steps (c) and (d), a position and/or orientation of at least one said orthodontic components with respect to the tooth it is associated with is changed with respect to a position and/or orientation, respectively, previously held.

18. The method according to claim 1, wherein in at least one of said repetitions of steps (c) and (d), the type of orthodontic component associated with at least one tooth is changed with respect to the orthodontic component previously associated with said tooth.

19. The method according to claim 18, wherein in at least one of said repetitions of steps (c) and (d), a position and/or orientation of at least one said orthodontic components with respect to the tooth it is associated with is changed with respect to a position and/or orientation, respectively, previously held.

20. A method for virtual orthodontic treatment using a computer system, comprising:

(a) providing a first virtual 3D model of teeth in a patient's jaw;

(b) selecting a virtual set of orthodontic components, comprising (i) brackets for attachment to teeth of the first virtual 3D model, and (ii) an archwire, each of the brackets having a slot for engaging the archwire;

(c) associating the brackets with the teeth of the first virtual 3D model so as to obtain a second virtual 3D model with the brackets positioned on the teeth of the first virtual 3D model;

(d) using a set of rules, including a rule that requires each slot to engage the archwire, computing the manner of movement of each tooth based at least partially on positioning of the bracket associated therewith, so as to obtain a resulting computed virtual 3D model of repositioned teeth following a virtual treatment;

(e) changing at least one bracket, the manner of associating a bracket with a tooth, the archwire shape, or a combination thereof, and repeating steps (c) and (d) one or more times until the resulting computed virtual 3D model of repositioned teeth following a virtual treatment represents a desired outcome of an orthodontic treatment; and (f) outputting the resulting computed virtual 3D model of repositioned teeth following a virtual treatment from the computer system.

* * * * *